United States Patent [19]

Labaire

[11] 4,037,273
[45] July 26, 1977

[54] EAR PROTECTOR

[76] Inventor: Wallace F. Labaire, 9 Pleasant St., Worcester, Mass. 01608

[21] Appl. No.: 588,596

[22] Filed: June 20, 1975

[51] Int. Cl.² .............................................. A41D 21/00
[52] U.S. Cl. ...................................................... 2/209
[58] Field of Search ....................... 2/209, 243 R, 425; 179/156, 182 R

[56] References Cited

U.S. PATENT DOCUMENTS

| | | | |
|---|---|---|---|
| 1,571,471 | 2/1926 | Galayda | 179/156 |
| 1,873,864 | 8/1932 | Ely | 2/209 UX |
| 2,447,470 | 8/1948 | Valentine | 179/182 R |
| 2,504,826 | 4/1950 | Goldman | 2/209 |
| 2,609,544 | 9/1952 | Berg | 2/209 |
| 2,898,596 | 8/1959 | Keen | 2/425 X |

FOREIGN PATENT DOCUMENTS

| | | | |
|---|---|---|---|
| 478,644 | 4/1927 | Germany | 179/156 |
| 150,163 | 7/1955 | Sweden | 2/209 |

*Primary Examiner*—Werner H. Schroeder
*Assistant Examiner*—Peter P. Nerbun
*Attorney, Agent, or Firm*—Norman S. Blodgett; Gerry A. Blodgett

[57] ABSTRACT

An ear protector for excluding foreign material and noxious noise from the ear. The ear protector includes two units attached to a head strap which encircles the head of the user. Each unit includes a rigid ring which encircles the ear of the user and to which the head strap is attached, a resilient ring coaxially mounted on the rigid ring, and a flexible container into which a rigid ring and resilient ring are hermetically sealed.

1 Claim, 4 Drawing Figures

EAR PROTECTOR

BACKGROUND OF THE INVENTION

Protection of the human ear from destructive influences such as loud noise, physical contact, and penetration by foreign substances, such as water and dirt, is an area which has only recently received the attention which it deserves. Because most ear injuries tend to detract from the enjoyment of life rather than cause extensive physical impairment, and bacause the causes of those ear injuries which normally do cause serious physical impairment were not known, historically little attention has been paid to protecting the ear. In recent years, however, considerable interest in ear protection has developed from a diverse range of sources. This interest has been brought about not only because of medical science's recognition that serious physical impairments can result from inner ear infections which in turn are sometimes caused by penetration of the ear by foreign material, but also due to more subtle influences in society. For example, people are no longer satisfied with the conclusion that disfigurements such as "cauliflower" ear are prices which participants in contact sports must pay, or that total or partial deafness are the price that workers in certain occupations must pay. This latter concept is most graphically expressed in the pioneering noise level standards set out by recent state and federal regulations concerning working conditions.

Because the various deleterious influences are normally not coexistent and because each one of them most commonly exists in a fairly specific environment, the development of protective devices for the various influences have developed more-or-less independently of one another. The first major category of ear protectors are ear plugs, which are small, resilient elements which are inserted directly into the ear canal. Ear plugs are primarily of value to keep foreign material (such as water or dust) out of the ears. If properly designed, they can also provide fairly effective protection against sound. The main advantages of ear plugs are that they are relatively inexpensive, that they are not cumbersome, and that they do not detract seriously from the appearance of the user. However, they can present sanitation problems, can be uncomfortable, and, because of their inconspicuousness, can cause some problems in the enforcement of their use.

The second major division of ear protectors are the yoke-type or earphone-type protectors. This type normally involves a pair of rigid cups each of which contains sound deadening material and is used in such a way as to surround the ear of the user. The cups are held in place by a U-shaped spring. The cups are connected to the ends of the spring and the bight of the spring or yoke passes over the top of the head of the user. The advantage of this system is that the device provides some protection to the outside of the ear, the device is relatively comfortable, and enforcement of use is relatively easy. The problems with this arrangement are that the device is easily displaced from the head and rendered inoperative, is relatively heavy and cumbersome, is relatively expensive, and does detract considerably from the appearance of the user.

The third basic type of ear protector is a helmet either of the soft or the hard variety. The soft helmet is normally made of flexible fabric and encloses the head of the user except for necessary openings. Normally, a resilient ring or pad is provided to surround or enclose the ears of the user. This type of arrangement is exemplified by the helmet used in wrestling or boxing. Although the main purpose in most applications is to protect the exterior of the ear from the type of contact which results in a cauliflower ear, enclosing pads also have the effect of attenuating noise and to some extent, excluding foreign material from the ear. Soft helmets are normally light in weight, and tend to stay in place, thus giving continuous protection to the user. On the other hand, they are normally expensive, uncomfortable to use, difficult to put on and take off, and have an ugly appearance. Hard helmets, which have a rigid shell enclosing the head of the user and a resilient inner layer to provide cushioning against the head, provide additional protection against physical contact, but are heavier and more awkward. These and other difficulties experienced with the prior art devices have been obviated in a novel manner by the present invention.

It is, therefore, an outstanding object of the invention to provide an ear protector which gives the ear suitable protection against physical contact, noise, and penetation by foreign matter.

Another object of this invention is the provision of an ear protector which is light in weight and is not cumbersome.

A further object of the present invention is the provision of an ear protector which minimizes its contact with the outside or inside of the ear both to increase comfort and reduce sanitary problems.

It is another object of the instant invention to provide an ear protector which is easy to put on and take off and yet is not easily, accidently displaced.

A still further object of the invention is the provision of an ear protector which minimizes detraction from the physical appearance of the user and yet is sufficiently conspicuous to allow easy enforcement of use.

It is a further object of the invention to provide an ear protector which is simple and inexpensive to manufacture.

It is a still further object of the present invention to provide an ear protector which can be completely emersed in liquid and is capable of being completely sanitized.

Another object of the invention is the provision of an ear protector which is made almost entirely of flexible materials so that the protector can be stored in a small space and under no circumstances can produce sharp rigid projections.

With these and other objects in view, as will be apparent to those skilled in the art, the invention resides in the combination of parts set forth in the specification and covered by the claims appended hereto.

SUMMARY OF THE INVENTION

This invention involves an ear protector for protecting the ears of a user from physical contact, loud noises, and penetration by foreign materials. The ear protector involves a head strap which surrounds the head of the user and two ear protector units, each attached to the strap and adapted to surround the outer portion of an ear. This unit consists of a rigid ring attached to the head strap and on which is mounted a resilient ring. The rings are hermetically sealed into a flexible container. Because the head strap is bifurcated and attached to widely-spaced portions of the rigid ring, the pressure exerted by the head strap on the ring is uniformly distributed around the outside of the ear.

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Figure 1:
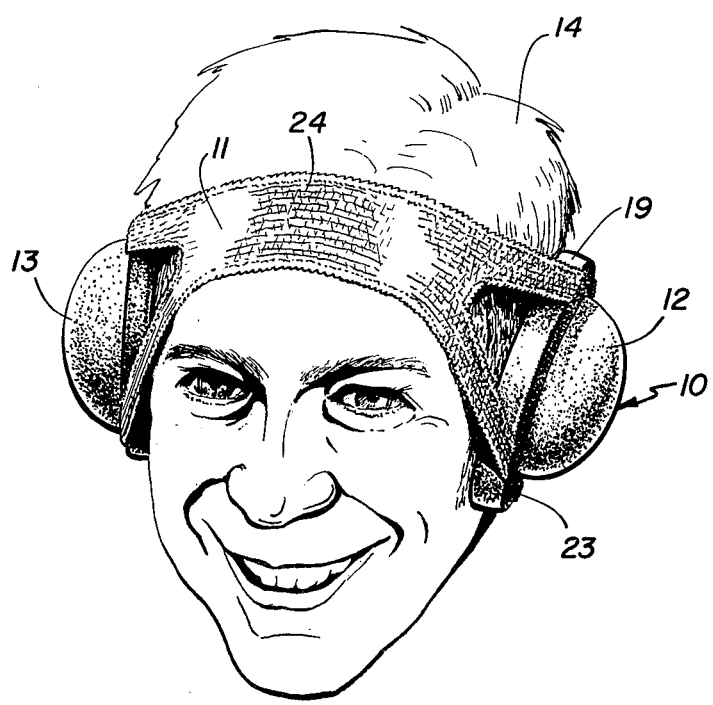
FIG. 1 is a perspective view of an ear protector embodying the principles of the present invention as it would appear in use on a human head.

Referring first to FIG. 1, in which are best shown the general features of the present invention, the ear protector, indicated generally by the numeral 10, is shown as having a head strap 11 and an ear protector unit 12. A second unit 13 is located on the other side of the head. In FIG. 1, the ear protector 10 is shown on the head of a user 14 with the ear protector unit 12 enclosing the outer ear of the user. Because the head strap 11 is elastic, the unit 12 is pressed snugly against the head forming a tight seal around the enclosed ear.

Figure 2:
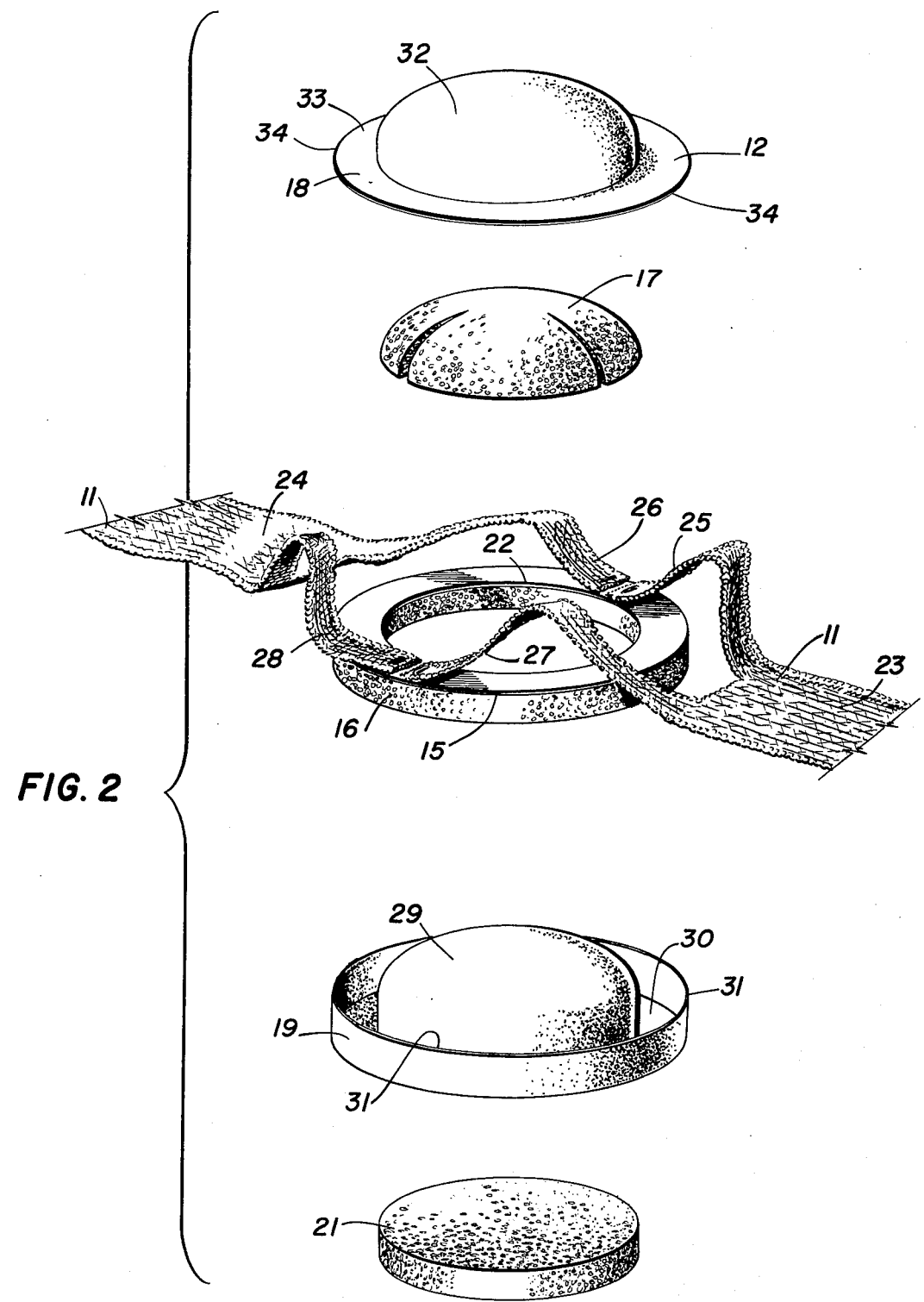
FIG. 2 is an exploded view of the various elements which make up the ear protector shown in FIG. 1.

FIG. 2 shows an exploded view of the head strap 11 and ear protector unit 12. The ear protector unit 12 includes a relatively rigid ring 15, a resilient 16, a permanent attenuating patch 17, an outer container 18, an inner container 19 and a temporary attenuating patch 21.

The rigid ring 15 is a thin, flat plate cut in an oval shape. The inner peripheral edge 22 has a major axis of 3 inches and a minor axis of 2 inches. The dimension is sufficient to surround the helix of the external portion of the human ear. In the preferred embodiment the rigid disk would be formed of plastic but metal might be substituted.

The head strap is composed of two portions, a rear portion 23 which extends around the back of the head of the user, and a front portion 24 which extends around the front, forehead of the user. In the vicinity of the ear protector units the portions of the head strap are bifurcated into strap ends 25, 26, 27, and 28. The strap ends are attached to the rigid ring so that the ends which are attached to the same portion of the head strap are approximately at diametrically-opposed positions on the ring. The head strap is formed of liquid immersible, elastic fabric of an open weave.

Also attached to the rigid ring is a resilient, plastic foam ring 16. The resilient ring 16 is attached concentrically to the inner (toward the users head) surface of the rigid ring 15.

The inner container 19 acts mainly to enclose the rigid ring 15 and the resilient ring 16. The inner container involves an outwardly (with respect to the user) or upwardly (as shown in FIG. 2) convex dome 29 surrounded by a peripheral upwardly or outwardly concave trough 30. At the extreme upper and outer peripheral edge of the trough is a sealing edge 31 which encircles the trough and dome. The inner container 19 is formed of a soft, thermoplastic material and is vacuum molded into shape so that the thickness of the upper portion of the dome 29 is considerably less than the walls of the trough.

The removable sound attenuating patch 21 is of oval shape corresponding to the shape of the dome 29. The patch 21, however, is slightly larger so that it fits into the dome with a friction fit. The patch 21 is formed of a resilient, foam plastic material.

The outer container 18 has a central dome 32 and a peripheral outwardly-directed rim 33. The outer container is formed of flexible, thermoplastic material similar to that from which the inner container 19 is formed. The outer container also has a peripheral outer sealing edge 34 which corresponds in shape and size to the sealing edge 31 of the inner container.

The permanent attenuating patch 17 is a piece of foam plastic shaped to conform to the surface of the dome 29 and the dome 32. The patch 17 would be permanently positioned between the aforementioned domes.

It should be noted that the permanent patch 17, the flexible ring 16, and the temporary patch 21 are all made of the same material. Likewise, the outer container 18 and the inner container 19 are made of the same material.

Figure 3:
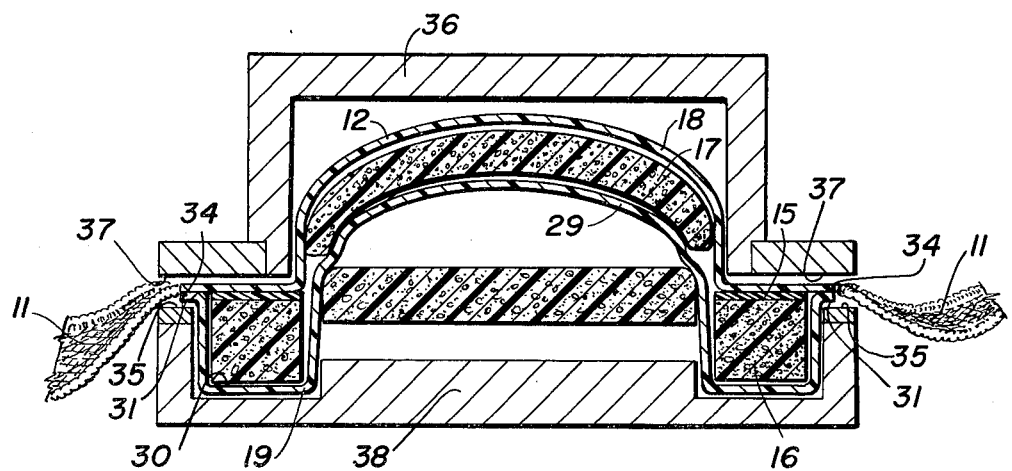
FIG. 3 is a sectional view through an ear protector unit and a sealing mold embodying the principles of the present invention.

A major asset of the present invention is the remarkable ease by which the individual components can be assembled into a final useful product. Initially the ends 25, 26, 27, and 28 of the head strap portions 23 and 24 are attached to the rigid rings 15 of each of the ear protector units 12 and 13. The flexible ring 16 is then attached to the rigid ring 15. Next, the temporary patch 21 is placed inside the dome 29 of the inner container 19. The inner container 19 is then placed in a first sealing mold 38 as shown in FIG. 3. The first sealing mold is provided with a peripheral first sealing surface 35 which lies adjacent the sealing edge 31 of the inner container 19.

Next, the assembly including the rigid ring 15, the resilient ring 16, and the head strap 11 is placed so that the resilient ring 16 is in the trough 30 of the inner container 19. The permanent patch 17 is then placed over the dome 29. The outer container 18 is placed over th permanent patch 17, so that the permanent patch 17 is within the dome 32 and the sealing edge 34 of the outer container 18 is correspondingly engaged to the sealing edge 31 of the inner container 19. A second sealing mold 36 is then placed over the outer container 18. A sealing surface 37 is provided on the sealing mold 36 and this sealing surface is positioned adjacent the sealing edge 34 of the outer container 18. Finally, heat is generated at the sealing surfaces 35 and 37 causing thermoplastic sealing of the sealing edges 31 and 34 together. In the preferred embodiment, the head straps 11 would be formed of an open mesh of elastic material so that the seal formed between the sealing edges 34 and 31 would pass through the head strap 11 to allow a hermetic seal around the entire edge.

Figure 4:
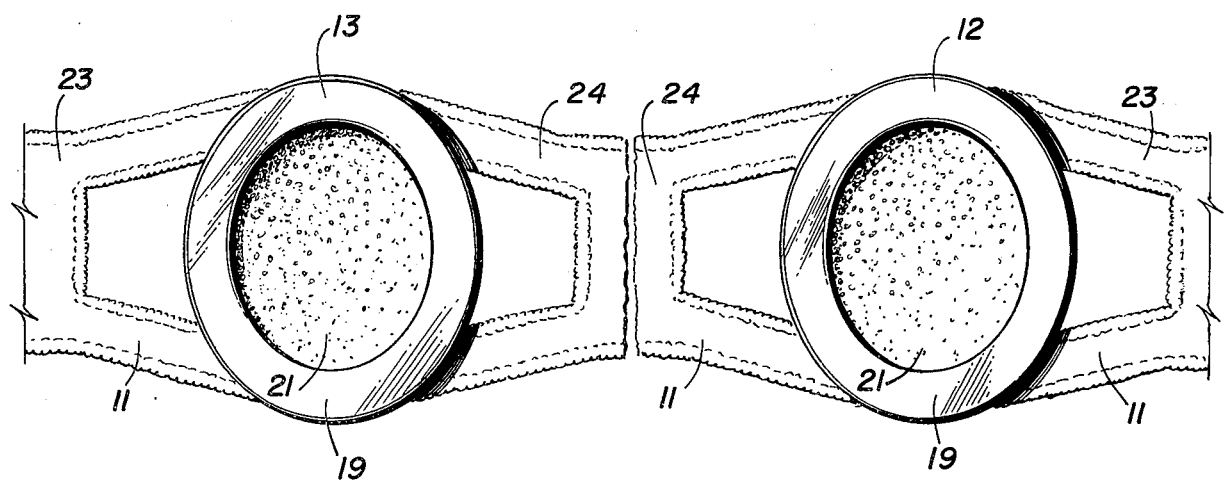
FIG. 4 is an elevation view showing the surfaces of the ear protector which would be in contact with the head of the user and the position of the head strap with respect to the ear protector units.

The ear protector unit 12 can then be removed from the molds and a similar operation carried out to form the ear protector unit 13. FIG. 4 shows a view of the completed head protector except that the head strap 11 would be continuous, including connection of portion 23.

FIG. 1 shows the preferred embodiment of the present invention in use on the head of a user 14. the head strap 11 is placed around the head with a portion 24 over the forehead and the portion 23 around the back of the head. The unit 12 is so placed that the inner container 19 surrounds and encloses the external ear of the user. Likewise, unit 13 would surround and enclose the other ear of the user.

Because the elastic strap surrounds the head of the user, the ear protector is securely held on the head and is not easily displaced. The tension on the ear protector units 12 and 13 caused by the elastic straps is distributed evenly around the periphery of the rigid ring because of the diametricaly-opposed positions of the connections between the head strap 11 and the rigid ring 15 and because the straps pass from the rigid ring at four widely spaced locations. This causes a uniform pressure throughout resilient pad 16 and the inner container 19 on the head of the user, around the ear. Thus, a good seal is formed around the ear against penetration by foreign material (including liquids and gases) without placing any pressure on the ear itself. Because the ear protector is formed almost entirely of soft material (with the exception of the completely enclosed rigid ring), the unit can be compressed to a relatively small size and does not contribute to injury should the user be exposed to physical contact. Because the ear protector is made entirely of light weight materials, the device itself is extremely light in weight and does not inhibit movement of the user. The ear protector is completely submersible in liquid either when used, or when being cleaned. The temporary patch 21 can be replaced should it become unsanitary. Additional sound attenuating material such as patches 21, can be added to increase the total sound attenuation of the ear protector, and the permanent patch 17 can be designed to suit the intended purpose.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. A method of forming an ear protector, comprising the steps of,
   a. forming an inner container having an inner, upwardly-convex dome and having a peripheral, upwardly-concave trough, the trough having an uppermost and outermost peripheral sealing edge,
   b. placing the inner container in a fist sealing mold, which mold has a sealing surface positioned adjacent and beneath the sealing edge of the inner container,
   c. concentrically connecting an annular resilient ring to a rigid ring,
   d. fixing a head strap to the rigid ring,
   e. placing the rigid ring with the resilient ring downwardly and concentrically in the trough of the inner container,
   f. placing a sound-damping material over the upwardly-facing surface of the dome of the inner container,
   g. forming an outer container having a sealing edge corresponding to the sealing edge of the inner container,
   h. placing the outer container in a second sealing mold which has a sealing surface positioned adjacent to and over the sealing edge of the outer container,
   i. bringing the first and second sealing mold together, so that the sealing edges of each container are in contact, except that a portion of the head strap passes between the sealing edges at predetermined locations, and
   j. causing the sealing surfaces to bring about a hermetic seal between the inner and outer containers at their sealing edges.

* * * * *